US012558501B2

(12) United States Patent
Cooper et al.

(10) Patent No.: US 12,558,501 B2
(45) Date of Patent: Feb. 24, 2026

(54) PORTABLE ELECTROMECHANICAL RESUSCITATOR BAG SINGLE SIDED COMPRESSION DEVICE

(71) Applicant: LIGAND INNOVATION GLOBAL LTD., Mississauga (CA)

(72) Inventors: Lisa Margaret Cooper, Toronto (CA); Gareth Alan Kenworthy, Stouffville (CA); Oladayo Emmanuel Olakulehin, Brampton (CA); Raymond John Minato, Toronto (CA)

(73) Assignee: LIGAND INNOVATION GLOBAL LTD., Mississauga (CA)

( * ) Notice: Subject to any disclaimer, the term of this patent is extended or adjusted under 35 U.S.C. 154(b) by 787 days.

(21) Appl. No.: 17/922,571

(22) PCT Filed: Apr. 30, 2021

(86) PCT No.: PCT/IB2021/053613
§ 371 (c)(1),
(2) Date: Oct. 31, 2022

(87) PCT Pub. No.: WO2021/220234
PCT Pub. Date: Nov. 4, 2021

(65) Prior Publication Data
US 2023/0181850 A1      Jun. 15, 2023

Related U.S. Application Data

(60) Provisional application No. 63/018,581, filed on May 1, 2020.

(51) Int. Cl.
*A61M 16/00* (2006.01)
*A61M 16/06* (2006.01)
(Continued)

(52) U.S. Cl.
CPC ...... *A61M 16/0084* (2014.02); *A61M 16/022* (2017.08); *A61M 16/06* (2013.01);
(Continued)

(58) Field of Classification Search
CPC ............ A61M 16/0084; A61M 16/022; A61M 16/06; A61M 2205/3331; A61M 16/20;
(Continued)

(56) References Cited

U.S. PATENT DOCUMENTS 3,548,821 A * 12/1970 Spiridonovich .. A61M 16/0045
128/205.14
3,782,371 A * 1/1974 Derouineau ......... A61H 31/007
601/41
(Continued)

FOREIGN PATENT DOCUMENTS

| CA | 3081940 A1 | 1/2020 |
| WO | 2011022112 A2 | 2/2011 |
| WO | 2019224810 A1 | 11/2019 |

OTHER PUBLICATIONS

International Search Report mailed Aug. 5, 2021, issued in corresponding PCT Application No. PCT/IB2021/053613, filed Nov. 4, 2021.

*Primary Examiner* — Brandy S Lee
*Assistant Examiner* — Tina Zhang
(74) *Attorney, Agent, or Firm* — PERRY + CURRIER INC.

(57) ABSTRACT

An example device comprises: a cradle to support a resuscitator bag; a paddle arm comprising: a paddle surface disposed opposite the cradle; and a pair of arms extending from the paddle surface; a housing comprising: top, bottom, front and rear sides, and an opening at the front side, towards the top side; the paddle surface extending through the opening; the pair of arms, of the paddle arm, rotatably attached to the housing at an end opposite the paddle surface (Continued)

towards the rear side; a nut assembly rotatably attached to the pair of arms therebetween; a screw threaded through the nut assembly; and a motor rotatably attached to the housing towards the bottom side of the housing; the motor configured to: drive the screw relative to the nut assembly to move the paddle arm towards and away from the cradle, to compress and release the resuscitator bag when located therebetween.

12 Claims, 8 Drawing Sheets

(51) Int. Cl.
  B33Y 80/00            (2015.01)
  G16H 40/63            (2018.01)
(52) U.S. Cl.
  CPC ..... G16H 40/63 (2018.01); *A61M 2205/3331* (2013.01); *B33Y 80/00* (2014.12)
(58) Field of Classification Search
  CPC ........ A61M 2016/0024; A61M 16/024; A61M 2016/0027; A61M 2205/103; A61M 2205/3561; A61M 2205/3584; A61M 2205/3592; A61M 2205/502; A61M 2205/52; A61M 2205/8206; A61M 2205/8237; A61M 2205/8262; A61M 2209/01; A61M 2209/084; A61M 16/0078; A61M 2202/0208; A61M 16/0057; A61M 16/0081; A61M 16/021; G16H 40/63; G16H 20/40; B33Y 80/00; G06N 20/00; F04B 45/067; F04B 45/027
  USPC ............ 417/412–413.1; 128/202.29, 204.21, 128/205.16
  See application file for complete search history.

(56)                    References Cited

U.S. PATENT DOCUMENTS

| | | | |
|---|---|---|---|
| 2005/0284472 A1* | 12/2005 | Lin | A61M 16/0084 |
| | | | 128/202.29 |
| 2009/0095300 A1* | 4/2009 | McMorrow | A61M 16/0045 |
| | | | 128/205.12 |
| 2014/0000613 A1* | 1/2014 | Hines | A61M 16/0081 |
| | | | 128/205.16 |
| 2017/0197047 A1 | 7/2017 | Minato et al. | |
| 2019/0232016 A1* | 8/2019 | Sayani | A61M 16/0003 |

* cited by examiner

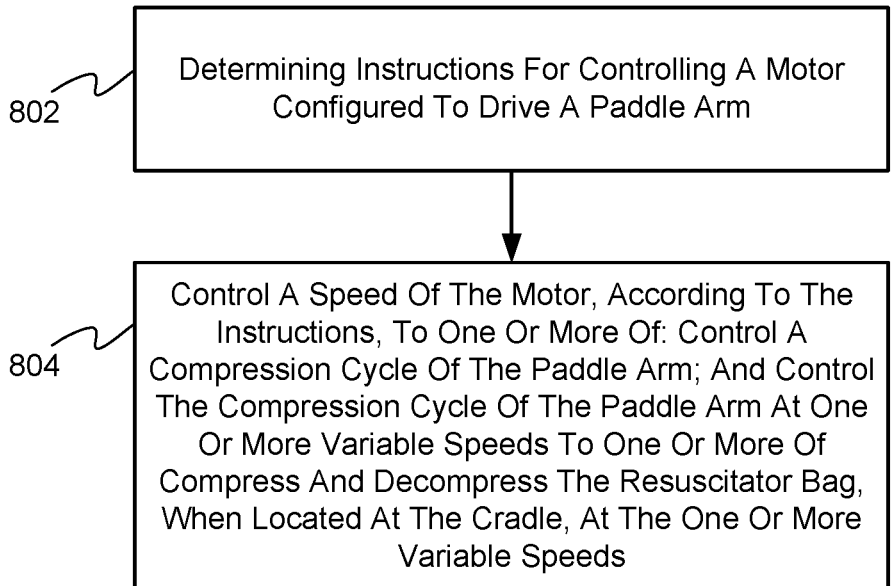

802

Determining Instructions For Controlling A Motor Configured To Drive A Paddle Arm

804

Control A Speed Of The Motor, According To The Instructions, To One Or More Of: Control A Compression Cycle Of The Paddle Arm; And Control The Compression Cycle Of The Paddle Arm At One Or More Variable Speeds To One Or More Of Compress And Decompress The Resuscitator Bag, When Located At The Cradle, At The One Or More Variable Speeds

PORTABLE ELECTROMECHANICAL RESUSCITATOR BAG SINGLE SIDED COMPRESSION DEVICE

BACKGROUND OF THE INVENTION

Ventilators and self-inflating resuscitator bags are utilized to provide positive pressure ventilation to patients that are unable to breath on their own. Ventilators are generally used in hospitals, while self-inflating resuscitator bags are generally used when a patient is being treated in the field or in transport to a hospital. Most ventilators are not generally suitable for the field as these devices are not portable. In resource limited countries, ventilators are not widely available, due to their high cost, and so medical personnel, and sometimes family members, have no alternative but to continuously manually compress a resuscitator bag to help patients to breath for long periods of time—from days to weeks at a time. Self-inflating resuscitator bags are manually compressed by one or more hands of medical personnel to provide positive pressure ventilation to a patient. One limitation of self-inflating resuscitator bags is that the manual compression of these bags renders it difficult for the medical personnel operating the bag to perform additional life-saving tasks, such as cardiopulmonary resuscitation (CPR) and the like. Another limitation of self-inflating resuscitator bags is that the manual compression of such bags by an operator is both fatiguing and renders it challenging for the operator to maintain a consistent rhythm and/or volume and/or pressure when compressing the bag. It is important for medical personnel, when operating self-inflating resuscitator bag, to maintain a consistent rhythm and/or volume and/or pressure of compressions to mimic the normal rhythm and/or volume and/or pressure of a person's breathing.

BRIEF DESCRIPTION OF THE SEVERAL VIEWS OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

FIG. 8 is a flowchart of a method for controlling a portable electromechanical resuscitator bag single sided compression device, in accordance with some examples.

Figure 1:
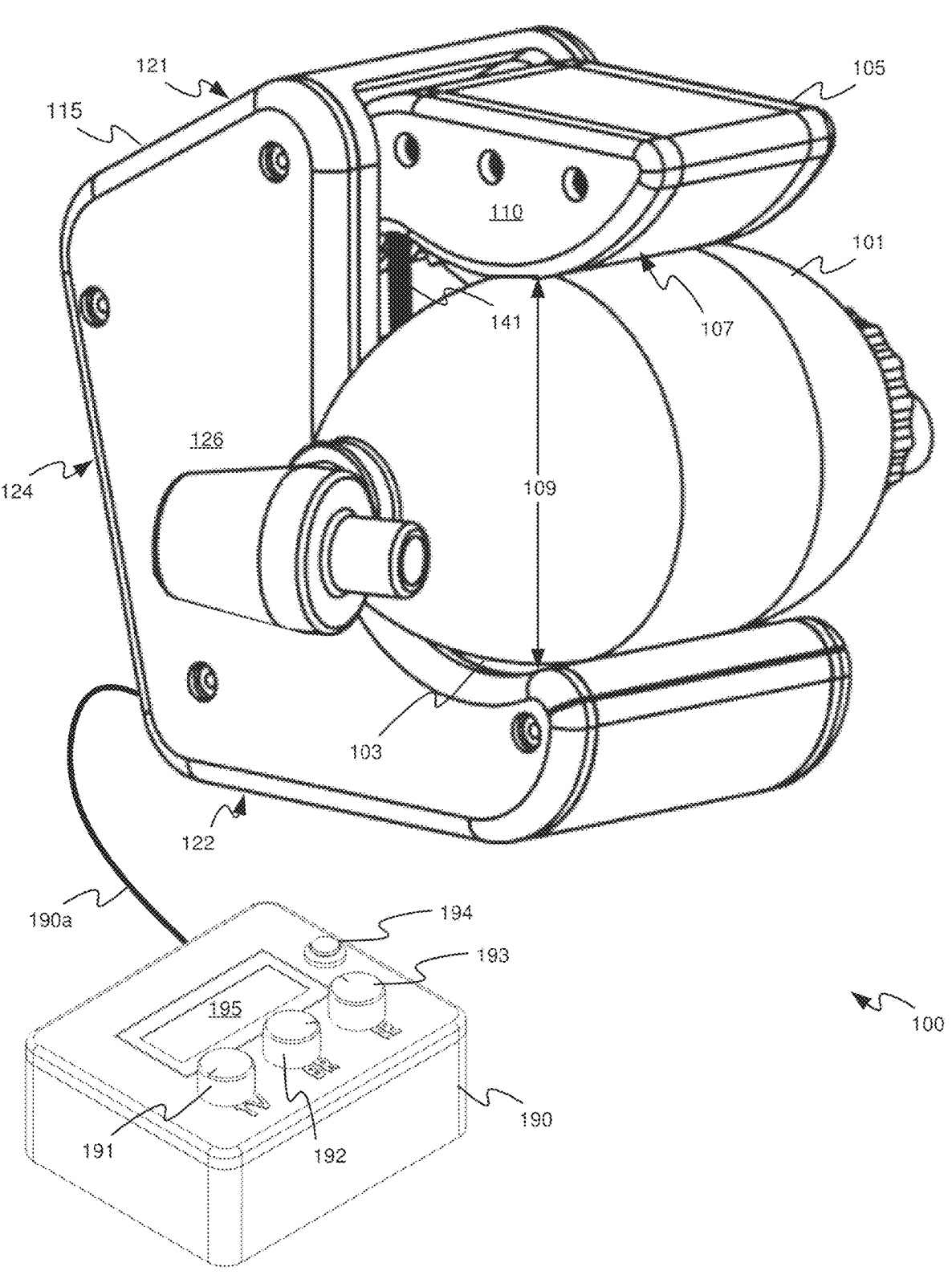
FIG. 1 depicts a perspective view of a portable electromechanical resuscitator bag single sided compression device, with a resuscitator bag located in a cradle thereof, in accordance with some examples.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION OF THE INVENTION

Provided herein is a device for compressing a resuscitator bag that is easy to manufacture, through traditional manufacturing techniques, and/or at least partially via three-dimensional printing. The device includes one paddle arm that is operated via a motor, a screw extending from the motor, and a nut assembly rotatably held in place between a pair of arms of the paddle arm, the screw being threaded through the nut assembly. The motor rotates in a first direction to turn the screw, which in turn interacts with the nut assembly to pull the paddle arm towards a cradle configured to hold a resuscitator bag, to compress the resuscitator bag; the motor rotates in a second direction, opposite the first direction to turn the screw, which in turn interacts with the nut assembly to push the paddle arm away from the cradle configured to decompress the resuscitator bag, which may be self-inflating. The paddle arm is rotatably attached to a housing of the device, via the pair of arms, at an end opposite a paddle surface, the nut assembly is located between the pair of arms and is rotatably attached therebetween, and the motor is rotatably attached to the housing. Due to the paddle arm rotating relative to the housing, the nut assembly rotating relative to the pair of arms, and the motor rotating relative to the housing, the paddle arm may be moved through a range of motion that would be challenging to achieve without using slot and pin assemblies, which are prone to jamming.

An aspect of the present specification provides a device comprising: a cradle; a paddle arm comprising: a paddle surface disposed opposite the cradle, a space between the paddle surface and the cradle for receiving a resuscitator bag therebetween, the cradle to support the resuscitator bag; and a pair of arms extending from the paddle surface; a housing comprising: a top side; a bottom side; a front side; a rear side; and an opening at the front side, towards the top side; the paddle surface extending through the opening at the front side; the pair of arms, of the paddle arm, rotatably attached to the housing at an end opposite the paddle surface towards the rear side; a nut assembly rotatably attached to the pair of arms therebetween; a screw threaded through the nut assembly; and a motor rotatably attached to the housing towards the bottom side of the housing; the motor configured to:

drive the screw relative to the nut assembly to move the paddle arm towards and away from the cradle, to compress and release the resuscitator bag when located therebetween.

Figure 2:
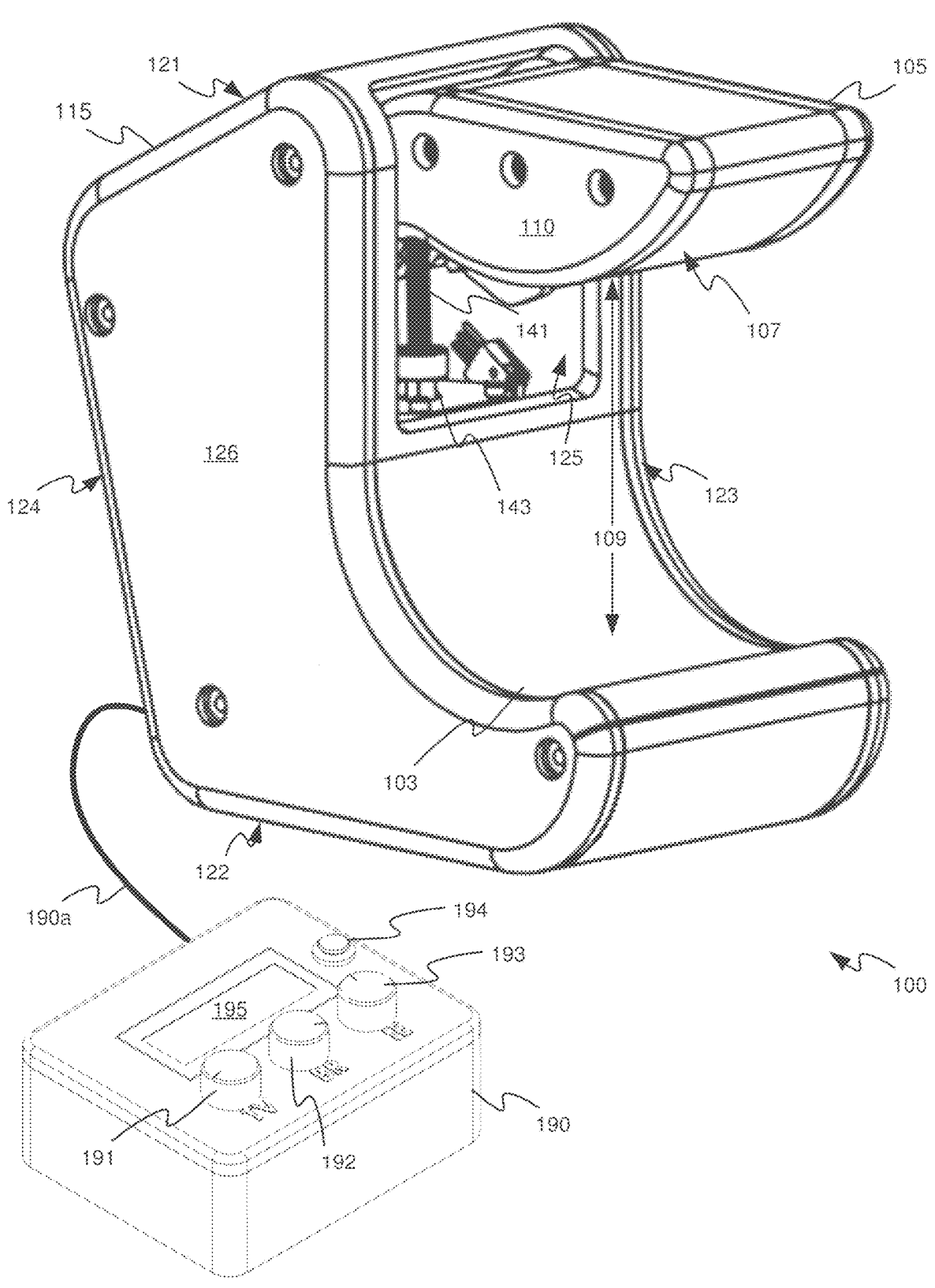
FIG. 2 depicts a perspective view of the device of FIG. 1 with the resuscitator bag removed, in accordance with some examples.
Figure 4:
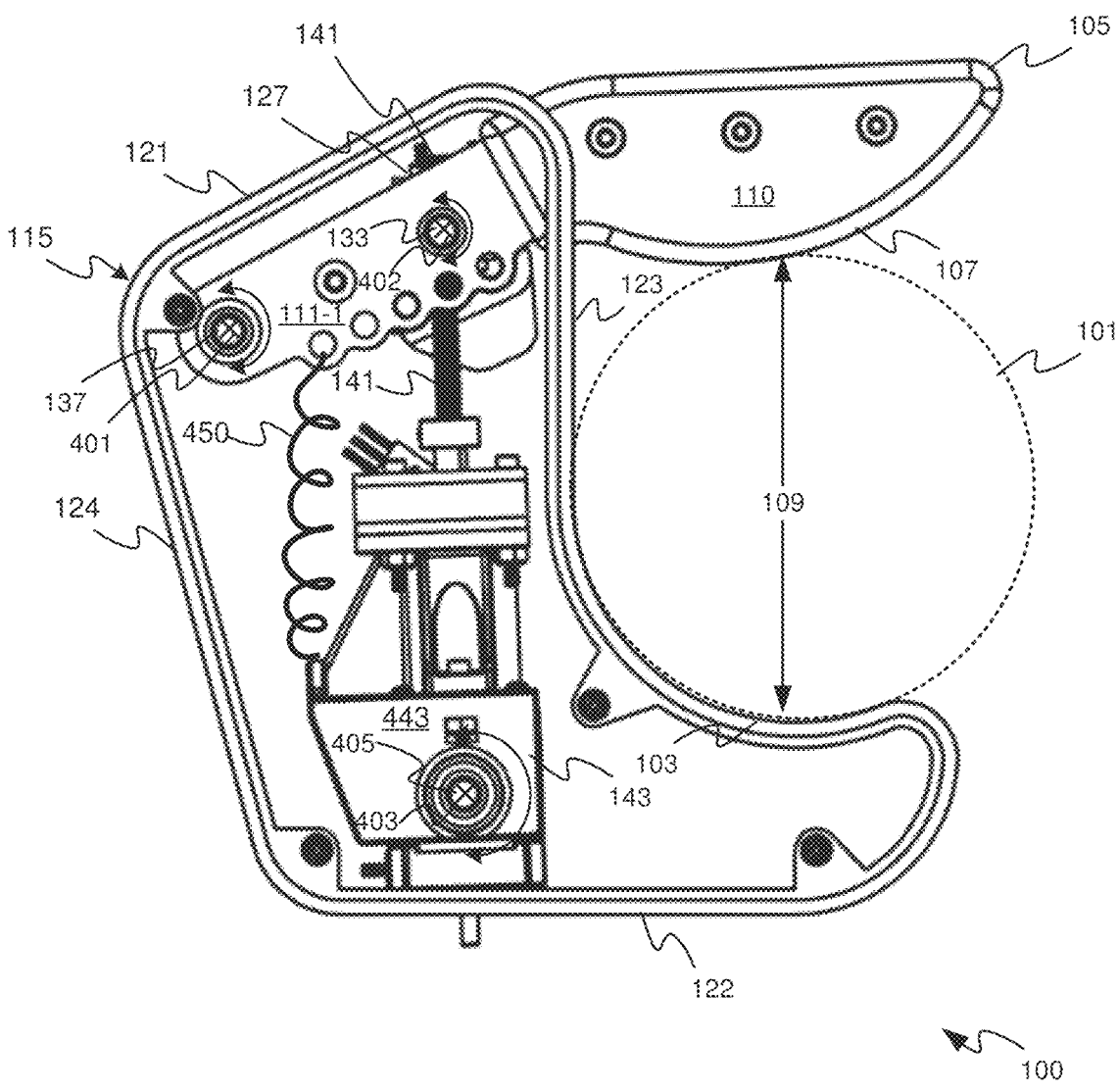
FIG. 4 depicts a side view of the device of FIG. 1, a side panel of a housing removed to show internal components, a paddle arm of the device being in a raised position, in accordance with some examples.
Figure 5:
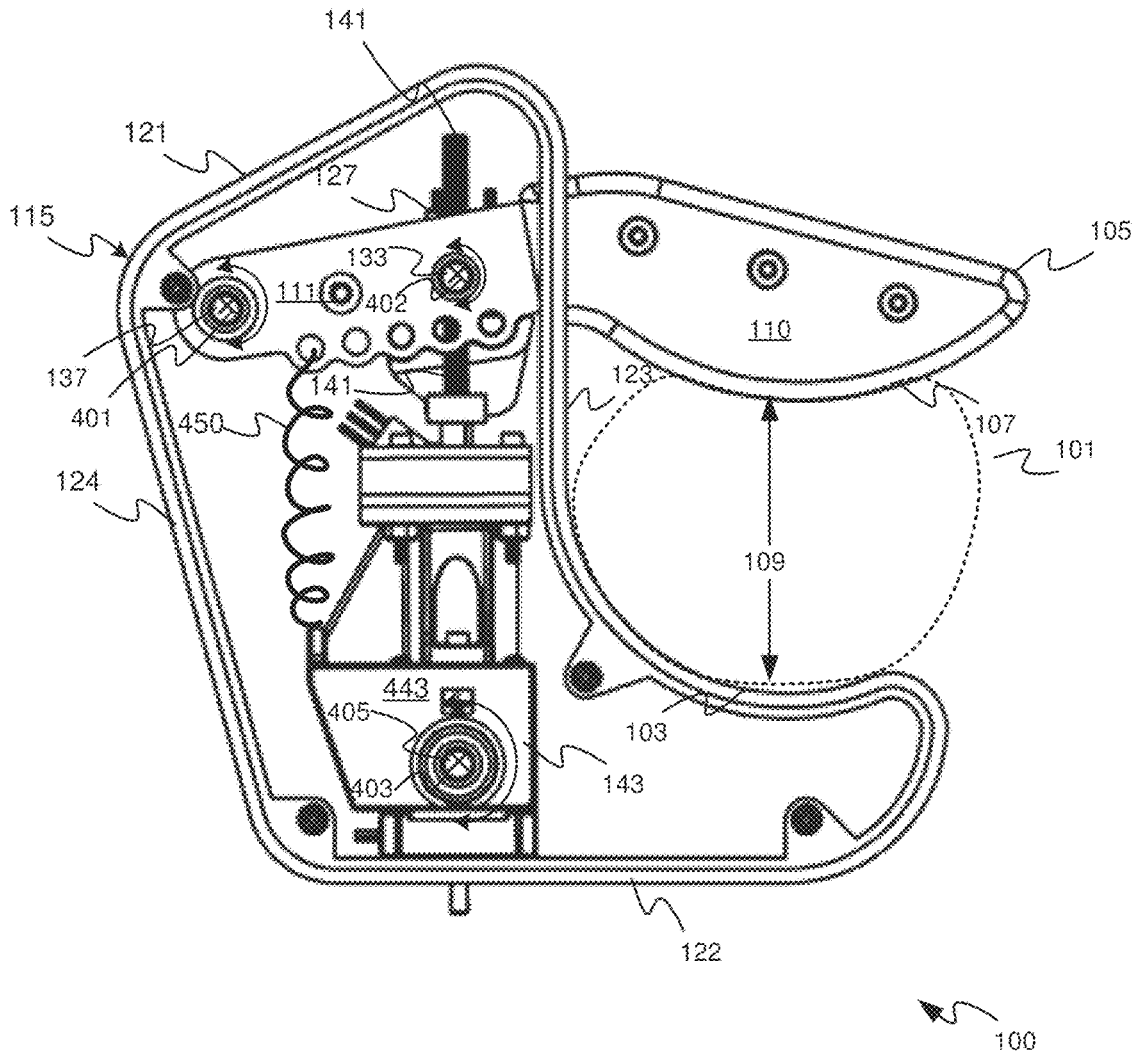
FIG. 5 depicts the side view of the device of FIG. 1, the side panel, and the paddle arm of the device being in an intermediate position, in accordance with some examples.
Figure 6:
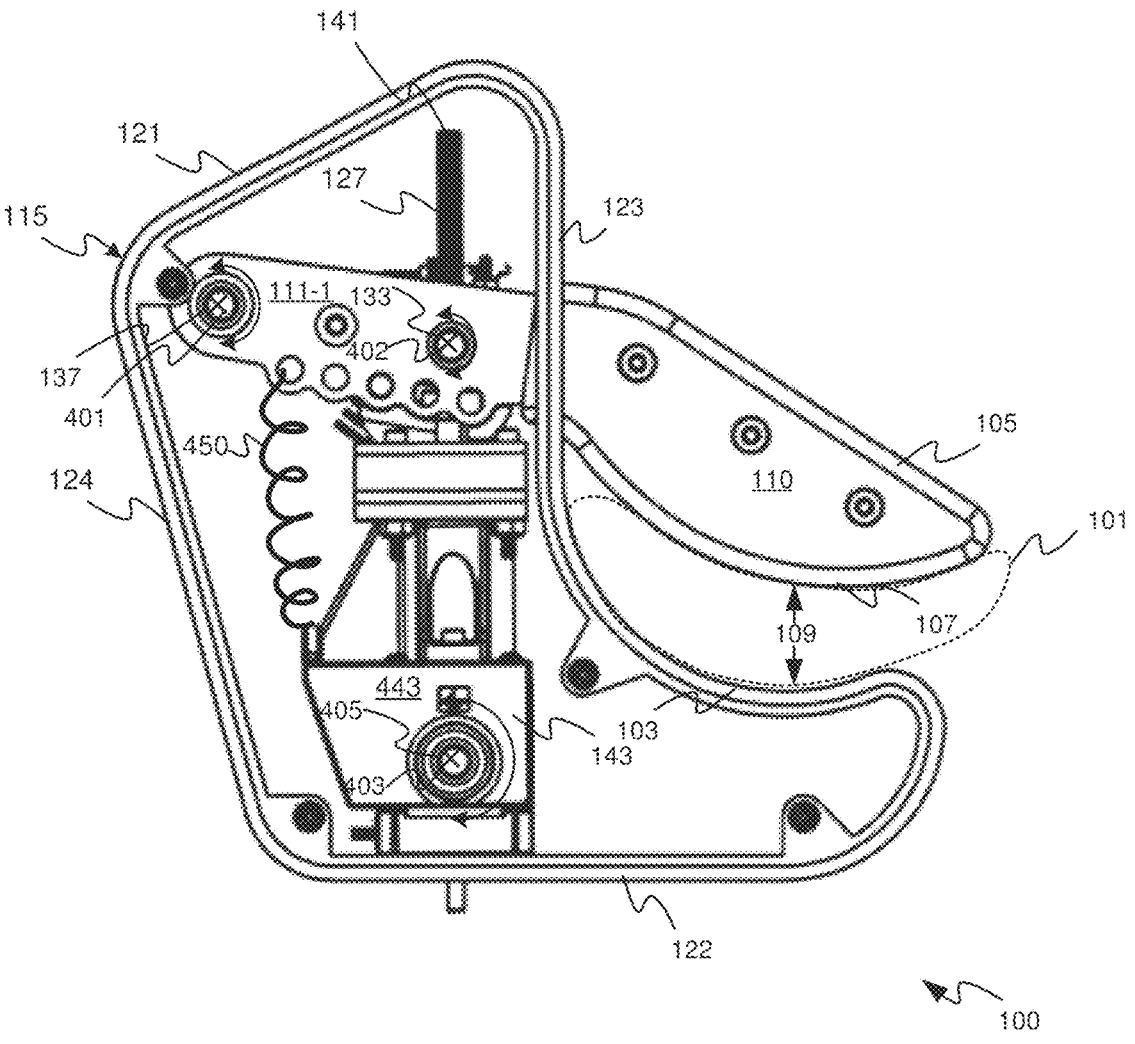
FIG. 6 depicts the side view of the device of FIG. 1, the side panel, and the paddle arm of the device being in a lower position, in accordance with some examples.

Attention is next directed to FIG. 1 and FIG. 2 which depicts a perspective view of a portable electromechanical resuscitator bag single sided compression device 100 (interchangeably referred to hereafter as the device 100). Further reference will be further made to FIG. 3A and FIG. 3B which depicts a perspective view of a paddle arm of the device 100 with and without a nut assembly. Reference will be further made to FIG. 4, FIG. 5 and FIG. 6 which depict a side view of the device 100 with a side panel removed to show internal components thereof, and a paddle arm in various respective positions.

Attention is first directed to FIG. 1 and FIG. 2. In FIG. 1, the device 100 holds a resuscitator bag 101, and in FIG. 2 the device 100 is depicted without the resuscitator bag 101. In general, the device 100 is configured to compress and release the resuscitator bag 101, which may comprise a self-inflating resuscitator bag 101. Such compression and release of the resuscitator bag 101 may be referred to as a compression cycle. While dimensions of the device 100 are not described herein, the dimensions may generally be selected for compatibility with the resuscitator bag 101, which may be a commercially available resuscitator bag; furthermore, different versions of the device 100 may be produced for respective compatibility with commercially available resuscitator bags of different dimensions (e.g. different radiuses, lengths, etc.).

The device 100 comprises a cradle 103 being of a shape and size to accept and hold the resuscitator bag 101. For example, as depicted, the cradle 103 has a shape at least partially complementary to a portion of the resuscitator bag 101, such that the resuscitator bag 101 may be placed into the cradle 103 and not roll out of the cradle 103 during the compression cycle. While not depicted, it is understood the resuscitator bag 101 may be connected to tubing that is in turn connected to a mask worn by a patient so that the resuscitator bag 101 may deliver air to the patient during the compression cycle via the tubing to assist the patient with breathing.

In general, the compression and release of the resuscitator bag 101 occurs via a paddle arm 105 which is controlled to move towards the cradle 103, to compress the resuscitator bag 101 when located in the cradle 103, and further controlled to move away from the cradle 103, to release the resuscitator bag 101. For example, as best seen in FIG. 1 and FIG. 2, the paddle arm 105 generally comprises a paddle surface 107 which is located opposite the cradle 103, with the resuscitator bag 101 located between the cradle 103 and the paddle surface 107 (e.g. when the resuscitator bag 101 has been loaded into the device 100). As the paddle arm 105 moves towards the cradle 103, the paddle surface 107 interacts with the resuscitator bag 101 to compress the resuscitator bag 101. Hence, the paddle surface 107 may generally have a curved and/or convex shape which extends towards the cradle 103 such that the curved and/or convex shape of the paddle surface 107 interacts with the resuscitator bag 101 without putting undo pressure at a single point of contact.

Put another away, the paddle surface 107 is generally disposed opposite the cradle 103, with a space 109 (as best seen in FIG. 2) between the paddle surface 107 and the cradle 103 for receiving the resuscitator bag 101 therebetween, the cradle 103 to support the resuscitator bag 101. Indeed, as depicted, the paddle surface 107 may be a surface of a paddle head 110 which may have a closed (as depicted)

or open structure, other than the paddle surface 107 which is generally a closed rigid structure (though the paddle surface 107 may alternatively comprise a rigid mesh, and/or the like; regardless the paddle surface 107 is generally rigid).

While not visible in FIG. 1 or FIG. 2, the paddle arm 105 further comprises a pair of arms 111-1, 111-2 extending from the paddle surface 107, for example into the device 100, as described in further detail below. The pair of arms 111-1, 111-2 are interchangeably referred to hereafter, collectively, as the pair of arms 111 and/or the arms 111, and, generically, as an arm 111. For example, brief reference is made to FIG. 3A and FIG. 3B which depict the pair of arms 111 extending from the paddle surface 107 (and/or the paddle head 110). Indeed, as depicted, the pair of arms 111 may be generally parallel and extend from the paddle surface 107 (and/or the paddle head 110) from opposing sides of the paddle surface 107 (and/or the paddle head 110). Put another way, the paddle surface 107 may be about parallel to a longitudinal axis 113 of the paddle arm 105, and portion of the paddle surface 107 that is closest to the cradle 103 may be about perpendicular to the longitudinal axis 113. In addition, when the resuscitator bag 101 is located in the cradle 103, the resuscitator bag 101 is about perpendicular to the longitudinal axis 113 (and/or about parallel to portion of the paddle surface 107 that is closest to the cradle 103).

Returning to FIG. 1 and FIG. 2, the device 100 further comprises a housing 115 comprising: a top side 121; a bottom side 1 opening 12522 (about opposite the top side 121); a front side 123; a rear side 124 (e.g. about opposite the front side 123); and an opening 125 at the front side 123, towards the top side 121. In general, the paddle surface 107 (and/or the paddle head 110) extends through the opening 125 at the front side 123. As will be described in more detail below, the pair of arms 111, of the paddle arm 105, is rotatably attached to the housing 115 at an end opposite the paddle surface 107 towards the rear side 124. In general, the front side 123 and the rear side 124 join the top side 121 to the bottom side 122. The housing 115 may further comprise lateral side panels 126 one of which is visible in FIG. 1 and FIG. 2, which join the sides 121, 122, 123, 124. As depicted, the side panels 126 may be removable. Furthermore, the sides 121, 122, 123, 124, as well as the side panels 126, may be of any suitable shape and/or configuration and/or the sides 121, 122, 123, 124, as well as the side panels 126 may comprise any suitable number of panels that may be assembled to form the housing 115 using screws, bolts and/or any other suitable types of fasteners and the like.

Furthermore, as also seen in FIG. 1 or FIG. 2, the housing 115 may comprise the cradle 103 and/or the cradle 103 may be integrated with the housing 115. For example, as depicted, the cradle 103 extends from the front side 123 of the housing 115, and is further located towards the bottom side 122 of the housing 115. However, in other examples, the cradle 103 may be a detachable and/or separate assembly, such that the cradle 103 is detachable from the housing 115.

Figure 3A:
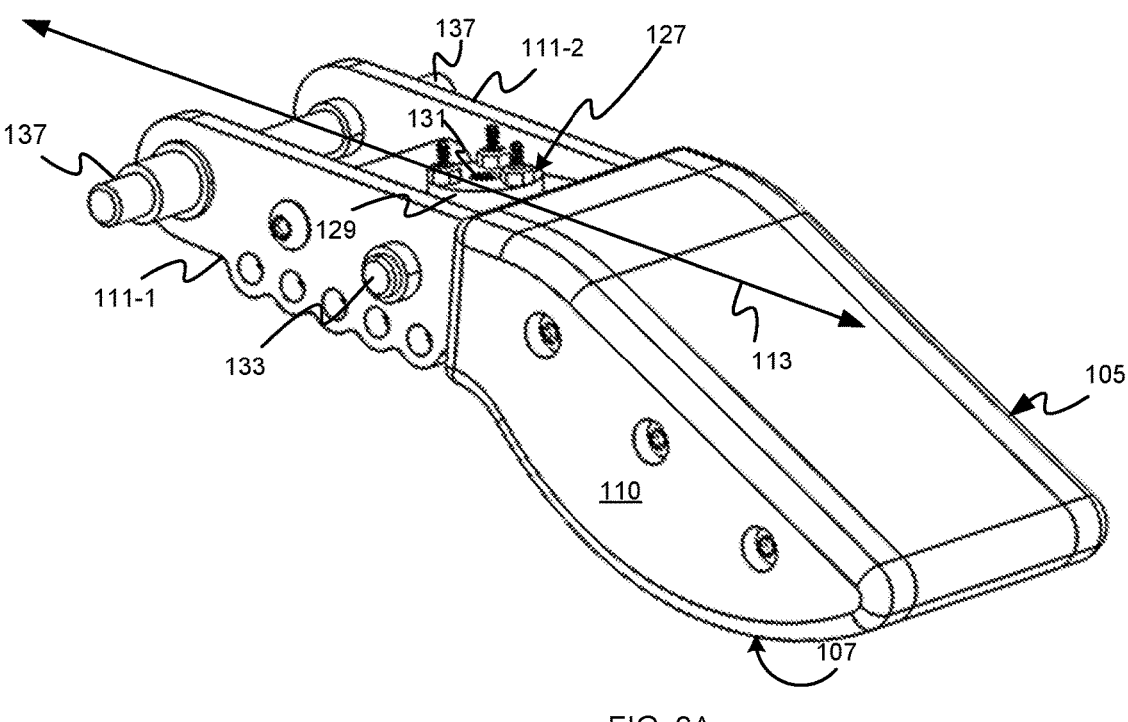
FIG. 3A depicts a perspective view of the paddle arm of the device of FIG. 1, with a nut assembly rotatably attached to a pair of arms extending from a paddle surface, in accordance with some examples.
Figure 3B:
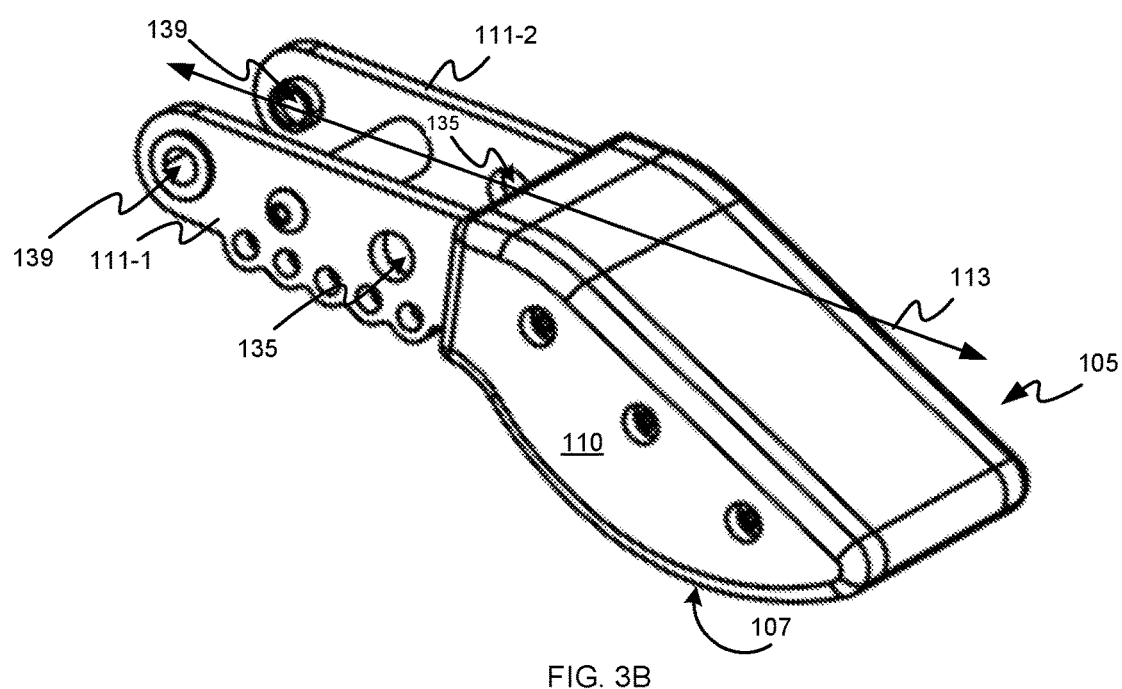
FIG. 3B depicts a perspective view of the paddle arm of the device of FIG. 1, with the nut assembly removed, in accordance with some examples.

While not visible in FIG. 1 or FIG. 2, and again with reference to FIG. 3A, the device 100 further comprises a nut assembly 127 rotatably attached to the pair of arms 111 therebetween. For example, the nut assembly 127 generally comprises a body 129 and a threaded hole 131 (e.g. a nut) through the body 129, into which a screw may be threaded (described below). The body 129 is generally located between the pair of arms 111 and is rotatably attached to the pair of arms 111 using spindles 133 and the like which may rotatably mate with respective cutouts 135, and the like in the pair of arms 111, to allow the nut assembly 127 to rotate and/or swing with respect to the pair of arms 111. An end of an example spindle 133 is depicted in FIG. 3A; while only one spindle 133 is visible, due to the perspective in FIG. 3A, it is understood that spindles 133 extend from opposite sides of the body 129 towards respective arms 111. Furthermore, as FIG. 3B is depicted with the nut assembly 127 removed from the paddle arm 105, the pair of cutouts 135 with which the spindles 133 mate are visible. While the cutouts 135 are depicted as being through the arms 111 (e.g. as an aperture), the spindles 133 held in place in the cutouts 135 via a boss, and the like on an outer end of the spindles 133 (e.g. at an external surface of the arms 111), in other examples, one or more of the cutouts 135 may comprise respective recesses into which a respective spindle 133 may snap, and the like (presuming a spindle 133 is at least partially flexible to deform enough to snap into a recess). However, any suitable combination of devices may be used to cause the nut assembly 127 to rotate relative to the arms 111; for example, the arms 111 may be assembled around the combination of the nut assembly 127 and the spindles 133.

FIG. 3A and FIG. 3B further depict that the paddle surface 107 and/or the paddle head 110 may, in some examples, be angled relative to the arms 111. For example, the paddle surface 107 and/or the paddle head 110 may be angled, relative to the arms 111, to control a size of the space 109 between the paddle surface 107 and the cradle 103.

Also depicted in FIG. 3A is a pair of spindles 137 that extend about perpendicular to the arms 111 (e.g. a spindle 137 for each arm 111) about which the paddle arm 105 rotates when attached to the housing 115. For example the spindles 137 (which may comprise a single spindle that extends through respective apertures 139 of the arms 111, as best seen in FIG. 3B where the spindles 137 are removed) may mate with respective cutouts (e.g. apertures and/or recesses) in the housing 115 and/or an internal frame of the housing 115, to allow the paddle arm 105 to rotate. The spindles 137 are generally located at an end of the paddle arm 105 that is opposite the paddle surface 107 and/or the paddle head 110, and the nut assembly 127 is located between the spindles 137 and the paddle surface 107 (and/or the paddle head 110).

Returning to FIG. 1 and FIG. 2, the device 100 further comprises a screw 141 threaded through the nut assembly 127; and a motor 143 rotatably attached to the housing 115 towards the bottom side 122 of the housing 115. The motor 143 is best seen in FIG. 2. FIG. 4, FIG. 5 and FIG. 6, and operation thereof will be described below with respect to FIG. 4, FIG. 5 and FIG. 6. However, the motor 143 is generally configured to: drive the screw 141 relative to the nut assembly 127 to move the paddle arm 105 towards and away from the cradle 103, to compress and release the resuscitator bag 101 when located therebetween. As the motor 143 drives the screw 141, the paddle arm 105 rotates relative to the housing 115, and the nut assembly 127 rotates relative to the arms 111, to allow for changes in angle of the screw 141 to the paddle arm 105 as the paddle arm 105 rotates. While a similar effect could be achieved with slot and pin assemblies, such slot and pin assemblies are prone to jamming and excessive wear (e.g. without complex linear friction management devices and/or linear bearings, which also adds to cost), as compared to a rotation of the nut assembly 127 relative to the arms 111. Furthermore, the motor 143 drives the screw 141, force is applied to the nut assembly 127 to rotate the paddle arm 105, as the nut assembly 127 translates force applied to the nut assembly 127 by the screw 141 to the paddle arm 105 to rotate the paddle arm 105 towards, and away from, the cradle 103. The motor 143 may comprise a stepper motor and the like, and/or any other suitable motor.

The motor 143 further rotates relative to the housing 115 to further allow for changes in angle of the screw 141, relative to the paddle arm 105 as the paddle arm 105 rotates.

Also depicted in FIG. 1 and FIG. 2 is an example input device 190 in communication with a controller of the device 100 (described below with respect to FIG. 7) via a wired connection 190a, though in other examples, the input device 190 may in communication with a controller of the device 100 via a wireless connection; alternatively, the input device 190, and the input device 190 may be integrated with the housing 115 of the device 100. As depicted, the input device 190 comprises physical buttons 191, 192, 193 for respectively adjusting and/or setting and/or controlling movement of the motor 143 according to tidal volume (e.g. "TV"), breath rate (e.g. "BR") and/or Inspiration/Expiration ratio (e.g. "IE"). Tidal volume may be understood to mean an amount of air volume that is delivered to a patient (e.g. by the resuscitator bag 101), a breath rate may be understood to mean a speed and/or rhythm of how quickly breaths are delivered to the patient and/or the frequency of the resuscitator bag 101 being compressed and released, and an inspiration/expiration ratio may be understood to mean a ratio of a time for an "inspiration" (e.g. inhale) breath to be delivered (e.g. by the resuscitator bag 101) versus an exhalation breath to be released (e.g. by the resuscitator bag 101). Hence, for example, the button 191 for adjusting and/or setting and/or controlling tidal volume may control a range of motion of the paddle arm 105 and/or the motor 143 (e.g. to control a distance that the paddle arm 105 moves towards the cradle 103 before being reversed, for example between a highest position as depicted in FIG. 4 and a lower position as depicted in FIG. 6); put another way, the button 191 may control a distance between a highest position, and the like, and a lower position of the paddle arm 105. Similarly, the button 192 for adjusting and/or setting and/or controlling breath rate may control a frequency of the paddle arm 105 (and/or the motor 143) as the paddle arm 105 is moved from a highest position (e.g. as depicted in FIG. 4), to a lower position (e.g. as depicted in FIG. 6) and back to the highest position (e.g. to control a frequency and/or rate with respect to breaths per minute, and the like). Similarly, the button 193 for adjusting and/or setting and/or controlling inspiration/expiration ratio may control a ratio of a time period that the paddle arm 105 is moved towards the cradle 103 by the motor 143, as compared to a respective time period that the paddle arm 105 is moved away from the cradle 103 by the motor 143. While reference is made to control of the paddle arm 105 it is understood that the buttons 191, 192, 193 control and/or adjust and/or setting the motor 143.

As depicted, the input device 190 further comprises a button 194 for starting a compression cycle, and a display device 195 for rendering and/or displaying the settings selected using the buttons 191, 192, 193 and/or any feedback from sensors, and the like of the device 100. For example, as described below, the device 100 may include a pressure sensor which may provide feedback on air delivered to a patient breathing via the resuscitator bag 101.

In some examples, the device 100 may not include an input device but rather may be controlled remotely via an external device (e.g. a computer, and the like) and/or the device 100 may store instructions for controlling the motor 143 in a manned that may not be adjustable.

Attention is next directed to FIG. 4, FIG. 5 and FIG. 6 which depict a side view of the device 100 with a side panel 126 removed to show the inner components of the device 100, and with the paddle arm 105 depicted in different positions, as described hereafter. For simplicity, in FIG. 4, FIG. 5 and FIG. 6, the device 100 is also depicted without the input device 190, however the input device 190 may nonetheless be present. A cross-section of the resuscitator bag 101 is further depicted in dashed lines to show location and compression thereof as the paddle arm 105 moves through the different positions. FIG. 4, FIG. 5 and FIG. 6 are otherwise similar to FIG. 1 and FIG. 2 with like components having like numbers.

FIG. 4 depicts the paddle arm 105 at a raised and/or highest position such that the space 109 is large enough to insert the resuscitator bag 101 therein. FIG. 4 further depicts an end view of a first axis 401 about which the paddle arm 105 rotates, as represented by a double ended "arced" arrow about the first axis 401, the first axis 401 being generally coincident with the spindles 137. In general, the first axis 401 is as far away from the paddle surface 107 and/or paddle head 110 as possible to maximize the diameter of a radius through which the paddle surface 107 and/or paddle head 110 rotates.

Similarly, FIG. 4 further depicts an end view of a second axis 402 about which the nut assembly 127 rotates, as represented by a double ended "arced" arrow about the second axis 402, the second axis 402 being generally coincident with the spindles 133. Similarly, FIG. 4 further depicts an end view of a third axis 403 about which the motor 143 rotates, as represented by a double ended "arced" arrow about the third axis 403, the third axis 403 being generally coincident with spindles 405 that extend from opposite sides of the motor 143 to mate with cutouts (not depicted); in some of the examples, the motor 143 may include a carriage from which the spindles 405 extend.

The axes 401, 402, 403 are about parallel with one another, and furthermore, the spindles 137, 405 generally mate with respective cutouts (not depicted), for example in the side panels 126 of the housing 115 (e.g. recesses in the housing 115) and/or an internal frame of the housing 115.

Hence, in general, FIG. 4 shows that, the pair of arms 111 may be rotatably attached to the housing 115 via a pair of spindles 137 extending from the pair of arms 111, the pair of spindles 137 mating with respective cutouts in one or more of the housing 115 and a frame of the housing 115. FIG. 4 (together with FIG. 3A and FIG. 3B) further shows that the nut assembly 127 may be rotatably attached to the pair of arms 111 via a pair of spindles 133 extending from the nut assembly 127, the pair of spindles 133 mating with respective cutouts 135 in the pair of arms 111. FIG. 4 further shows that the motor 143 may be rotatably attached to the housing 115 via a pair of spindles 405 extending from the motor 143, and specifically, as depicted, the pair of spindles 405 may extend from a chassis 443 of the motor 143. While not depicted, the pair of spindles 405 are generally understood to mate with respective cutouts in in one or more of the housing 115 and a frame of the housing 115.

In some examples, as also depicted in FIG. 4, the device 100 may further comprise at least one spring 450, and the like, to bias the paddle arm 105 towards a the cradle 103 (and/or a lower position, as depicted in FIG. 6) to assist the motor 143 with lowering the paddle arm 105 towards the cradle 103. For example, as depicted, in FIG. 4, at least one spring 450 extends from the chassis 443 of the motor 143 to the arm 111-1 of the paddle arm 105; indeed, the least one spring 450 may include a first spring 450, as depicted, extending from the chassis 443 to the arm 111-1, and a second spring 450 (not depicted), extending from the chassis 443 to the arm 111-2 (e.g. the springs 450 arranged about symmetrically about an center plane and/or axis extending between the top side 121 and the bottom side 122 of the housing 115, though the at least spring 450 may be arranged in any suitable manner and/or the at least one spring 450 may include any suitable number of springs 450 and/or the at least one spring 450 may be attached to any suitable location(s) of the paddle arm 105, other than the arms 111). Furthermore, while the at least one spring 450 is depicted as extending from the chassis 443 and the paddle arm 105, the at least one spring 450 may extending from any other suitable location of the device 101 and the paddle arm 105 including, but not limited to, an interior of the housing 115 and the paddle arm 105. Further aspects of the at least one spring 450 will be described in more detail below.

Attention is next directed to FIG. 5 which depicts the paddle arm 105 in an intermediate position, lowered towards the cradle 103 to compress the resuscitator bag 101, which is schematically shown, in dashed lines, as being compressed relative to FIG. 4. For example, in FIG. 5, the motor 143 has rotated the screw 141 to pull the paddle arm 105 towards the cradle 103 via the nut assembly 127. The paddle arm 105 has rotated about the first axis 401, the nut assembly 127 has rotated about the second axis 402, and the motor 143 has rotated (slightly) about the third axis 403. Furthermore, the at least one spring 450 is depicted as being shorter than in FIG. 4, indicating that the at least one spring 450 has assisted the motor 143 in pulling the paddle arm 105 towards the cradle 103.

Attention is next directed to FIG. 6 which depicts the paddle arm 105 in a lowered position and/or lowest position, further lowered towards the cradle 103 to compress the resuscitator bag 101, which is schematically shown, in dashed lines, as being compressed relative to FIG. 5. For example, in FIG. 6, the motor 143 has rotated the screw 141 to further pull the paddle arm 105 towards the cradle 103 via the nut assembly 127. The paddle arm 105 has further rotated about the first axis 401, the nut assembly 127 has further rotated about the second axis 402, and the motor 143 has further rotated (slightly) about the third axis 403. Furthermore, the at least one spring 450 is depicted as being shorter than in FIG. 5, indicating that the at least one spring 450 has assisted the motor 143 in pulling the paddle arm 105 towards the cradle 103.

Hence, FIG. 4, FIG. 5 and FIG. 6 show a sequence in time as the motor 143 moves the paddle arm 105 towards the cradle 103 to compress the resuscitator bag 101, and further, FIG. 6, FIG. 5 and FIG. 4 (e.g. in reverse) show a sequence in time as the motor 143 moves the paddle arm 105 away the cradle 103 to release the resuscitator bag 101, which self-inflates. It is understood that as a direction of movement of the paddle arm 105 changes (e.g. from being pulled towards the cradle 103 to being moved and/or pushed away from the cradle 103, or vice versa), a direction of rotation of the screw 141 and/or the motor 143 changes.

Furthermore, as the resuscitator bag 101 is self-inflating, the resuscitator bag 101 will generally resist compression as the paddle arm 105 compresses the resuscitator bag 101, for example by applying an opposing force to the paddle arm 105 during compression of the resuscitator bag 101; conversely, the self-inflation of the resuscitator bag 101 will cause the resuscitator bag 101 to apply an assisting force to the paddle arm 105 as the paddle arm 105 releasees the resuscitator bag 101, which generally assists the motor 143 in moving the paddle arm 105 away from the cradle 103 during release of the resuscitator bag 101. The opposing and assisting forces are generally a same force that opposes or assists movement of the paddle arm 105 depending on a direction of movement of the paddle arm 105, and which generally depends on a stiffness, and the like, of the resuscitator bag 101. Such a situation may lead to the motor 143 exerting higher force and/or torque on the screw 141 during compression than during release, and which can hence also lead to sudden changes in force and/or torque on the paddle arm 105 when changing between compression and release (e.g. as a direction of movement of the paddle arm 105 changes and/or as a rotational direction of the screw 141 and/or motor 143 changes). However, the at least one spring 450 generally mediates such a situation, by applying a spring force which generally opposes the force applied to the paddle arm 105 by the resuscitator bag 101. In particular, in some examples, a spring constant of the at least one spring 450 may be selected such that the motor 143 applies a similar force and/or torque to the screw 141 throughout the compression cycle, and/or the force and/or torque applied by the motor 143 may be reduced, relative to when the at least one spring 250 is not present. Hence, the spring constant selected for the at least one spring 450 may depend on a stiffness of the resuscitator bag 101: for example, for relatively stiffer resuscitator bags, a relatively higher spring content of the at least one spring 450 may be selected, as compared to a spring content of the at least one spring 450 selected for relatively less stiff resuscitator bags; indeed, a spring constant of the at least one spring 450 may be selected for a particular type of resuscitator bag that has a given stiffness. Furthermore, use of the at least one spring 450 generally reduces the overall forces and/or torques applied by the motor 143 to compress the resuscitator bag 101; hence, a smaller motor 143 (e.g. in size and/or power) may be used when the at least one spring 250 is present, as compared to a motor used when the at least one spring 250 is present, which may lead to less power being used by the device 100 and/or a the device 100 being more compact (e.g. as motors that consume less power tend to be smaller relative to motors that consume more power).

In particular, the device 100 is further understood to comprise a controller which may control the motor 143 to rotate the screw 141 to raise or lower the paddle arm 105 according to a compression cycle where rates and/or speeds of compression and/or release may be constant and/or may vary, for example according to one or more of tidal volume, breath rate, inspiration/expiration ratio, and the like.

Figure 7:
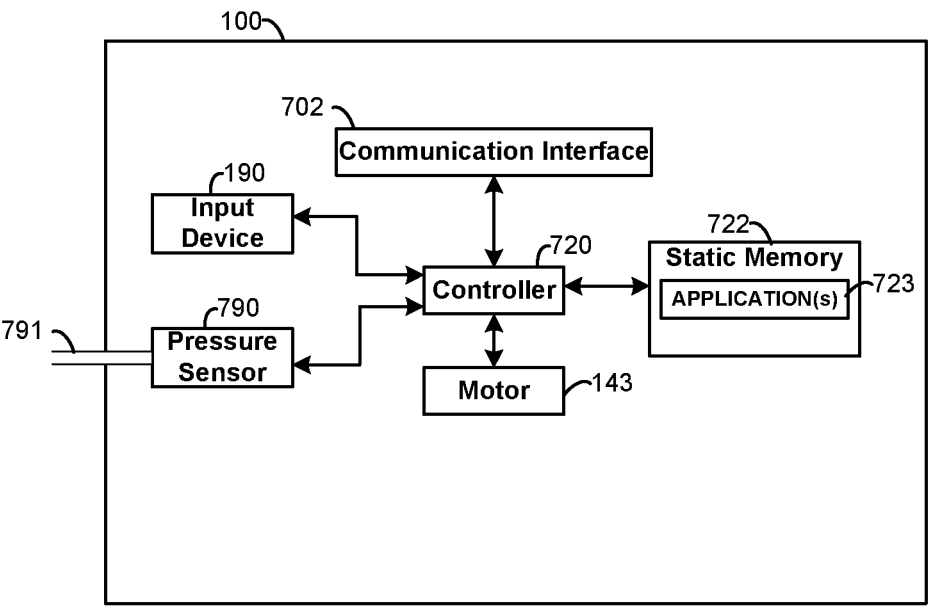
FIG. 7 is a device diagram showing a device structure of a portable electromechanical resuscitator bag single sided compression device, in accordance with some examples.

For example, attention is next directed to FIG. 7 which depicts a schematic block diagram of an example of the device 100.

As depicted, the device 100 comprises: the motor 143, the input device 190 (which though depicted as internal to the device 101 may be external, as in FIG. 1 and FIG. 2 and/or the input device 190 may be optional), a communication interface 702, a controller 720, and a static memory 722 storing at least one application 723. Hereafter, the at least one application 723 will be interchangeably referred to as the application 723. The controller 720 is generally coupled to the motor 143, the communication interface 702, and the static memory 722.

As depicted, the device 100 further includes an optional pressure sensor 790 connected to an optional tube 791 which may in turn be used to tap into, and/or be connected to, tubing from the resuscitator bag 101 to a mask worn by a patient. In particular the optional tube 791 may tap into, and/or be connected to, tubing proximal the resuscitator bag 101 and/or the mask, and/or the optional tube 791 may tap into, and/or be connected to, the mask. Hence, the pressure sensor 790 may sense air pressure being delivered to the patient by the resuscitator bag 101 and/or, pressure changes in the tubing and/or the mask caused by the patient (e.g. when the patient attempts to inhale and/or exhale). In some of these examples, the compression cycle of the paddle arm 105 may be controlled in a feedback loop with pressure sensed by the pressure sensor 790, for example to maintain and/or achieve given pressures during the compression cycle (e.g. the pressure may change during the compression cycle due to inspiration/inhalation and/or exhalation, and the pressure sensor 790 may be used to control the paddle arm 105 to attempt to achieve one or more given pressures and the like). Alternatively, the pressure sensor 790 may be used to detect when a patient attempts to inhale and/or exhale such that the paddle arm 105 may be controlled to assist with such inhalation/inspiration and/or exhalation.

While not depicted, the device 100 may further include a code Read Only Memory (ROM), for storing data for initializing system components, and a Random-Access Memory (RAM) coupled to the controller 720. The device 100 may comprise any other suitable components including, but not limited to, a batteries, a battery charger, a connector to a mains power supply, a voltage regulator, a motor controller (e.g. which may convert data representing control of tidal volume, breath rate, inspiration/expiration ratio to motor control pulses and/or signals, and the like), a safety circuit, a real-time clock, and/or any other suitable components, and the like. Furthermore, the device 100 may including one or more limiting switches for limiting a range of motion of the paddle arm 105.

The communication interface 702 may include one or more wired and/or wireless input/output (I/O) interfaces for receiving instructions for operating the motor 143, including, but not limited to, an Ethernet interface, a serial bus interface, a Bluetooth™ interface, a WiFi™, and the like.

The controller 720 may include ports (e.g. hardware ports) for coupling to other hardware components.

The controller 720 may include one or more logic circuits, one or more processors, one or more microprocessors, and/or the controller 720 may include one or more ASIC (application-specific integrated circuits) and one or more FPGA (field-programmable gate arrays), and/or another electronic device. In some examples, the controller 720 and/or the device 100 is not a generic controller and/or a generic device, but a device specifically configured to implement functionality for controlling the motor 143 For example, in some examples, the device 100 and/or the controller 720 specifically comprises a computer executable engine configured to implement functionality for controlling the motor 143.

The static memory 722 is a non-transitory machine readable medium that stores machine readable instructions to implement one or more programs or applications. Example machine readable media include a non-volatile storage unit (e.g. Erasable Electronic Programmable Read Only Memory ("EEPROM"), Flash Memory) and/or a volatile storage unit (e.g. random-access memory ("RAM")). In the example of FIG. 2, programming instructions (e.g., machine readable instructions) that implement the functional teachings of the device 100 as described herein are maintained, persistently, at the memory 722 and used by the controller 720 which makes appropriate utilization of volatile storage during the execution of such programming instructions.

In particular, the memory 722 stores instructions corresponding to the at least one application 723 that, when executed by the controller 720, enables the controller 720 to implement functionality for controlling the motor 143 including, but not limited to, some or all of the blocks of the method set forth in FIG. 8.

In illustrated examples, when the controller 720 executes the one or more applications 723, the controller 720 is enabled to control the motor 143 and in particular control a speed of the motor 143 to one or more of: control a compression cycle of the paddle arm 105; and control the compression cycle of the paddle arm 105 at one or more variable speeds to one or more of compress and decompress the resuscitator bag 101, when located at the cradle 103, at the one or more variable speeds, for example to control one or more of tidal volume, breath rate, inspiration/expiration ratio, and the like. In some examples, the application 723 may include instructions for controlling the motor 143; in other examples, the application 723 may include a plurality of instructions for controlling the motor 143 according to one or more different compression cycle "recipes" and/or algorithms for example to control one or more of tidal volume, breath rate, inspiration/expiration ratio, and the like (e.g. and a user of the device 100 may select from the recipes to control the motor 143). In other examples, when the controller 720 executes the one or more applications 723, the controller 720 may be further enabled to: determine instructions for controlling the motor 143; and control a speed of the motor 143 according to the instructions to one or more of: control a compression cycle of the paddle arm 105; and control the compression cycle of the paddle arm 105 at one or more variable speeds to one or more of compress and decompress the resuscitator bag, when located at the cradle, at the one or more variable speeds.

The application 723 may include numerical algorithms configured for controlling the motor 143. Alternatively, and/or in addition to numerical algorithms, and/or programmed algorithms, predetermined algorithms, and/or static algorithms, the application 723 may include machine learning models and/or algorithms, and the like, which have been trained to control the motor 143.

Furthermore, in these examples, the application 723 may initially be operated by the controller 720 in a training mode to train the machine learning models and/or algorithms of the application 723 to perform the above described functionality and/or generate classifiers therefor.

The one or more machine learning models and/or algorithms of the application 723 may include, but are not limited to: a deep-learning based algorithm; a neural network; a generalized linear regression algorithm; a random forest algorithm; a support vector machine algorithm; a gradient boosting regression algorithm; a decision tree algorithm; a generalized additive model; evolutionary programming algorithms; Bayesian inference algorithms, reinforcement learning algorithms, and the like. However, generalized linear regression algorithms, random forest algorithms, support vector machine algorithms, gradient boosting regression algorithms, decision tree algorithms, generalized additive models, and the like may be preferred over neural network algorithms, deep learning algorithms, evolutionary programming algorithms, and the like, in some medical environments. Any suitable machine learning algorithm and/or deep learning algorithm and/or neural network is within the scope of present examples.

Attention is now directed to FIG. 8, which depicts a flowchart representative of a method 800 for controlling the motor 143. The operations of the method 800 of FIG. 8 correspond to machine readable instructions that are executed by the device 100, and specifically the controller 720 of the device 100. In the illustrated example, the instructions represented by the blocks of FIG. 8 are stored at the memory 722 for example, as the application 723. The method 800 of FIG. 8 is one way in which the controller 720 and/or the device 100 may be configured. Furthermore, the following discussion of the method 800 of FIG. 8 will lead to a further understanding of the device 100, and its various components.

The method 800 of FIG. 8 need not be performed in the exact sequence as shown and likewise various blocks may be performed in parallel rather than in sequence. Accordingly, the elements of method 800 are referred to herein as "blocks" rather than "steps." The method 800 of FIG. 8 may be implemented on variations of the device 100 of FIG. 1, as well.

At a block 802, the controller 720 and/or the device 100 determines instructions for controlling the motor 143. For example, the instructions may be preprogrammed at the application 723. Alternatively, a plurality of sets of instructions may be preprogrammed at the application 723, and an input device and/or the communication interface 702 may be used to select one of the plurality of sets of instructions (which may be selected via a menu in graphic user interface (GUI) and the like), to select a compression cycle "recipe" and/or algorithm. Alternatively, a specific set of instructions may be received an input device and/or the communication interface 702 to define a compression cycle "recipe" and/or algorithm for the motor 143. Regardless, the instructions generally define a speed and/or speeds at which the motor 143 is to rotate the screw 141 to control the paddle arm 105 to compress and/or release the resuscitator bag 101 for example to control one or more of tidal volume, breath rate, inspiration/expiration ratio, and the like. The instructions may specify constant and/or variable speeds at which the motor 143 is to rotate the screw 141 to control the paddle arm 105 to compress and/or release the resuscitator bag 101.

At a block 804, the controller 720 and/or the device 100 controls the motor 143 according to the instructions to control a speed of the motor 143 to one or more of: control a compression cycle of the paddle arm 105; and control the compression cycle of the paddle arm 105 at one or more variable speeds to one or more of compress and decompress the resuscitator bag 101, when located at the cradle 103, at the one or more variable speeds.

In some examples where pressure is monitored by the pressure sensor 790, the method 800 may further comprise the controller 720 and/or the device 100 controlling the motor 143 to drive the screw 141 to compress and release the resuscitator bag 101, via the paddle arm 105, in a feedback loop with pressure sensed by the pressure sensor 790. For example, the feedback loop may be used to control movement of the paddle arm 105 to achieve one or more given pressures as sensed by the pressure sensor 790. Such a feedback loop may be used to change and/or adjust and/or control one or more of tidal volume, breath rate, inspiration/exhalation ration, and the like.

In further examples where pressure is monitored by the pressure sensor 790, the method 800 may further comprise the controller 720 and/or the device 100 controlling the motor 143 to drive the screw 141 to compress and release the resuscitator bag 101, via the paddle arm 105, responsive to a given pressure change sensed by the pressure sensor. For example, when a patient starts to inhale (or exhale), a given pressure change may occur in tubing and/or a mask that is sensed by the pressure sensor 790, and the controller 720 and/or the device 100 may responsively control the motor 143 to drive the screw 141 to compress and release the resuscitator bag 101, via the paddle arm 105, to assist with the inhalation and/or to synchronize movement of the paddle arm 105 with the attempted breathing of the patient.

Indeed, by controlling the compression cycle of the paddle arm 105 to one or more of compress and decompress the resuscitator bag 101, a tidal volume delivered by the resuscitator bag 101 may be controlled. However, the instructions may be further used to control one or more of: a breath per minute and/or breathing rate of a patient whose breathing is controlled via the resuscitator bag 101 (e.g. by controlling a rate of the compression cycle); an inhalation-to-expiration ratio (e.g. by controlling a time of a compression portion of a compression cycle relative to a time of a release portion of a compression cycle).

In yet further examples, the device 100 may be provided with a valve at a mask worn by a patient whose breathing is controlled via the resuscitator bag 101, the air of the resuscitator bag 101 being delivered via the mask.

Furthermore, various components of the device 100 may be produced using traditional manufacturing techniques and/or three-dimensional printing, for example to more quickly produce the device 100 during times of crisis and/or when resuscitator devices are in high demand.

Furthermore, while certain features have been described for locating, holding in place and rotating the components of the device 100, any suitable combination of components may be used to locating, holding in place and rotating the features of the device 100 including, but not limited to, bosses, nuts, pins, and the like.

In the foregoing specification, specific embodiments have been described. However, one of ordinary skill in the art appreciates that various modifications and changes may be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

In this document, language of "at least one of X, Y, and Z" and "one or more of X, Y and Z" may be construed as X only, Y only, Z only, or any combination of two or more items X, Y, and Z (e.g., XYZ, XY, YZ, XZ, and the like). Similar logic may be applied for two or more items in any occurrence of "at least one . . . " and "one or more . . . " language.

Moreover, in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment may be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it may be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

What is claimed is:

1. A device comprising:

a cradle;

a paddle arm comprising:

a paddle surface disposed opposite the cradle, a space between the paddle surface and the cradle for receiving a resuscitator bag therebetween, the cradle to support the resuscitator bag; and a pair of arms extending from the paddle surface;

a housing comprising: a top side; a bottom side; a front side; a rear side; and an opening at the front side, towards the top side; the paddle surface extending through the opening at the front side; the pair of arms, of the paddle arm, rotatably attached to the housing at an end opposite the paddle surface towards the rear side;

a nut assembly rotatably attached to the pair of arms therebetween;

a screw threaded through the nut assembly; and a motor rotatably attached to the housing towards the bottom side of the housing; the motor configured to:

drive the screw relative to the nut assembly to move the paddle arm towards and away from the cradle, to compress and release the resuscitator bag when located therebetween.

2. The device of claim 1, further comprising:

a controller configured to control the motor.

3. The device of claim 1, further comprising a controller configured to control the motor to control a speed of the motor to one or more of:

control a compression cycle of the paddle arm; and control the compression cycle of the paddle arm at one or more variable speeds to one or more of compress and decompress the resuscitator bag, when located at the cradle, at the one or more variable speeds.

4. The device of claim 1, wherein the housing comprises the cradle extending from the front side of the housing, towards the bottom side of the housing.

5. The device of claim 1, wherein the pair of arms is rotatably attached to the housing via a pair of spindles extending from the pair of arms, the pair of spindles mating with respective cutouts in one or more of the housing and a frame of the housing.

6. The device of claim 1, wherein the nut assembly is rotatably attached to the pair of arms via a pair of spindles extending from the nut assembly, the pair of spindles mating with respective cutouts in the pair of arms.

7. The device of claim 1, wherein the motor is rotatably attached to the housing via a pair of spindles extending from the motor, the pair of spindles mating with respective cutouts in in one or more of the housing and a frame of the housing.

8. The device of claim 1, further comprising:

a controller configured to control the motor; and a pressure sensor configured to detect pressure at one or more of a tube and a mask connected to the resuscitator bag, the controller configured to control the motor to drive the screw to compress and release the resuscitator bag in a feedback loop with pressure sensed by the pressure sensor.

9. The device of claim 1, further comprising:

a controller configured to control the motor; and a pressure sensor configured to detect pressure at one or more of a tube and a mask connected to the resuscitator bag, the controller configured to control the motor to drive the screw to compress and release the resuscitator bag responsive to a given pressure change sensed by the pressure sensor.

10. The device of claim 1, further comprising:

at least one spring configured to bias the paddle arm towards the cradle.

11. The device of claim 1, further comprising:

at least one spring extending between a chassis of the motor and the paddle arm, the at least one spring configured to bias the paddle arm towards the cradle.

12. The device of claim 1, further comprising:

at least one spring extending between an interior of the housing and the paddle arm, the at least one spring configured to bias the paddle arm towards the cradle.

* * * * *